(12) United States Patent
Lewis et al.

(10) Patent No.: US 9,775,855 B2
(45) Date of Patent: Oct. 3, 2017

(54) COMPOSITIONS COMPRISING MACROLIDE AND TETRACYCLINE AND THEIR USES

(76) Inventors: Thomas J. Lewis, Talbott, TN (US);
Clement L. Trempe, Nahant, MA (US)

( * ) Notice: Subject to any disclaimer, the term of this patent is extended or adjusted under 35 U.S.C. 154(b) by 192 days.

(21) Appl. No.: 14/344,502

(22) PCT Filed: Sep. 13, 2012

(86) PCT No.: PCT/US2012/055160
§ 371 (c)(1),
(2), (4) Date: Mar. 10, 2015

(87) PCT Pub. No.: WO2013/040206
PCT Pub. Date: Mar. 21, 2013

(65) Prior Publication Data
US 2015/0190415 A1 Jul. 9, 2015

Related U.S. Application Data
(60) Provisional application No. 61/534,822, filed on Sep. 14, 2011.

(51) Int. Cl.
| | | |
|---|---|---|
| *A61K 31/65* | (2006.01) |
| *A61K 31/7048* | (2006.01) |
| *A61K 45/06* | (2006.01) |
| *A61K 31/198* | (2006.01) |
| *A61K 31/424* | (2006.01) |
| *A61K 31/43* | (2006.01) |
| *A61K 31/433* | (2006.01) |
| *A61K 31/4409* | (2006.01) |
| *A61K 31/496* | (2006.01) |
| *A61K 31/4965* | (2006.01) |
| *A61K 31/59* | (2006.01) |
| *A61K 33/00* | (2006.01) |
| *A61K 35/60* | (2006.01) |
| *A61K 31/19* | (2006.01) |

(52) U.S. Cl.
CPC .......... *A61K 31/7048* (2013.01); *A61K 31/19* (2013.01); *A61K 31/198* (2013.01); *A61K 31/424* (2013.01); *A61K 31/43* (2013.01); *A61K 31/433* (2013.01); *A61K 31/4409* (2013.01); *A61K 31/496* (2013.01); *A61K 31/4965* (2013.01); *A61K 31/59* (2013.01); *A61K 31/65* (2013.01); *A61K 33/00* (2013.01); *A61K 35/60* (2013.01); *A61K 45/06* (2013.01)

(58) Field of Classification Search
CPC ........................... A61K 31/65; A61K 31/7048
USPC ........................................................ 514/152
See application file for complete search history.

(56) References Cited

U.S. PATENT DOCUMENTS 6,884,784 B1 * 4/2005 Mitchell .............. A61K 31/192
514/152

OTHER PUBLICATIONS

Giacometti et al., "In-vitro activity of macrolides alone and in combination with artemisin, atovaquone, dapsone, minocycline or pyrimethamine against Cryptosporidium parvum", Journal of Antimicrobial Chemotherapy, vol. 38, No. 3, pp. 399-408 (1996).*

* cited by examiner

*Primary Examiner* — Kevin E Weddington
(74) *Attorney, Agent, or Firm* — Verrill Dana LLP; Wayne A. Keown

(57) ABSTRACT

The present invention provides for methods, compositions, and kits pertaining to the treatment of various diseases associated with inflammation. In various aspects, the invention provides methods and compositions comprising an effective amount of a macrolide and an effective amount of a tetracycline.

3 Claims, No Drawings

COMPOSITIONS COMPRISING MACROLIDE AND TETRACYCLINE AND THEIR USES

FIELD OF THE INVENTION

The invention relates to compositions and methods with action on multiple cellular activities and pathways, such as those relevant to cardiovascular, neurological and/or neurodegenerative disorders and/or diseases of accelerated aging. For instance, a combination therapy of an effective amount of a tetracycline derivative and an effective amount of a macrolide derivative is provided.

BACKGROUND

Diseases of aging are a leading cause of functional limitation among older adults worldwide and will continue to ascend in global health importance as populations continue to age and effective cures remain elusive. C D Mathers and D Loncar (2006) Projections of global mortality and burden of disease from 2002 to 2030. *PLoS Med,* 3(11), e442. A leading class of aging diseases is neurological disorders. A recent study estimated that over 2.5 million Americans suffered from Alzheimer's disease (AD), and nearly 4 million had that and other forms of dementia in 2002. Plassman et al. (2007) Prevalence of Dementia in the United States: The Aging, Demographics, and Memory Study. Neuroepidemiology, 29, 125-132. Given expected increases in the size of the older adult population those numbers are expected to increase dramatically by 2050. Alzheimer's Association. (2009) Alzheimer's disease facts and figures. *Alzheimer's & Dementia,* 5(3).

Many diseases of aging have long asymptomatic incubation periods followed by a progression into disability and poor health with concomitant large and continual financial costs to the individual, families, insurance companies, and the healthcare system. Further, particularly for the neurological and/or neurodegenerative and neuromuscular diseases, and even cardiovascular diseases, the standard of care is palliative at best. Therefore, new treatments for neurological and/or neurodegenerative and/or cardiovascular disorders are needed.

BRIEF DESCRIPTION OF THE INVENTION

Accordingly, the present invention provides for methods and compositions that are more effective for treatment of diseases including neurological and/or neurodegenerative disorders, and/or cardiovascular disorders, and inflammation that is often present in association.

In some aspects, the present invention relates to compositions with action on multiple cellular activities and pathways. One formulation comprises an effective amount of a tetracycline derivative and an effective amount of a macrolide derivative. Further, methods for treating or preventing disease comprising the administration of an effective amount of this composition are included. In some embodiments, the invention also involves the use of supplements and vitamins for the purpose of, inter alia, enhancing the human immune system and improving a subject's response to treatment. In some embodiments, the formulations comprise vitamin D and/or fish oil and/or cod liver oil and/or other sources of EPA and DHA such as, but not limited to, Krill oil. In other embodiments, the formulations include N-acetyl cysteine (NAC). In other embodiments, the formulations include Augmentin and/or Diamox and/or Rifater.

In some embodiments, the diseases treated with the disclosed compositions are degenerative and chronic diseases of aging. The present inventors have discovered that a broad range of aging diseases have overlapping risk factors and thus possess similar and/or overlapping antecedents or root-causes. In most, if not all, cases inflammation is present as detected through a variety of means including biomarkers and blood tests. These diseases present differently based on the complex and unique phenotype of the individual with the disease including, but not limited to any combination of: immune system health (innate and acquired), age, medical history, lifestyle, nutrition, acute and chronic exposures, environmental factors, and genetics. This invention relates to the treatment of diseases of aging such as those that delay or prevent the onset and/or progression of these diseases and may well reverse the disease process, affording the patient a normal and healthy lifespan.

In one aspect, the invention includes a method of treating a disease associated with inflammation, the method comprising administering an effective amount of a macrolide and an effective amount of a tetracycline to a patient in need thereof.

In some embodiments, the invention includes a method of treating a disease associated with inflammation, the method comprising administering an effective amount of a macrolide, wherein the macrolide is selected from the group consisting of clarithromycin (e.g. Biaxin) and roxithromycin and an effective amount of a tetracycline, wherein the tetracycline is minocycline or doxycycline to a patient in need thereof.

In various embodiments, the methods of the present invention further comprise administering an effective amount of cod liver oil and/or an effective amount of fish oil and/or other sources of EPA and DHA such as, but not limited to, Krill oil. In some embodiments, the methods of the present invention further comprise administering an effective amount of vitamin D. In various other embodiments, the methods of the present invention further comprise administering an effective amount of Augmentin and/or Diamox and/or Rifater and/or N-acetyl cysteine (NAC).

In various embodiments, the methods of the present invention further comprise a disease selected from: Addison's disease; ALS (Lou Gehrig's Disease); Alzheimer's disease; amyloidosis; angina; rheumatoid arthritis; arthritis; asthma; atherosclerosis; auto immune disease; bronchiectasis; cancer; cardiac arrythmias; cardiac failure; cardiomyopathy; cardiovascular diseases; chronic fatigue syndrome; chronic obstructive pulmonary disorder; chronic renal disease; coronary artery disease; Crohn's disease; dementia(s); diabetes (II); diabetes insipidus; diabetes mellitus type 1, diabetes mellitus type 2; diseases of infections; diseases of inflammation/inflammatory disorders; diseases of intracellular infections; diseases of obligate intracellular infections, dysrhythmias; endocarditis; epilepsy; fungal diseases; giant cell arteritis; glaucoma; haemophilia; heart failure; hyperhomocysteinemia; hyperlipidaemia; hypertension; hypothyroidism; inclusion body myotosis; leukocyte defects; Lewy body dementia; lipid imbalance (total cholesterol: HDL is about 3:1 or, preferably, less); lupus; Lyme disease; multiple sclerosis; myopathies; neurological and/or neurodegenerative diseases; neuromuscular diseases; Parkinson's disease; peripheral vascular disease; polymyalgia rheumatica; rheumatoid arthritis; schizophrenia; systemic lupus erythematosus; taupathies; ulcerative colitis; vasculitis; viral diseases and Whipple's disease.

In another aspect, the invention includes a pharmaceutical composition comprising an effective amount of a macrolide and an effective amount of a tetracycline.

In one embodiment, the invention provides a pharmaceutical composition comprising an effective amount of minocycline and clarithromycin.

In another embodiment, the invention provides a pharmaceutical composition comprising an effective amount of minocycline and roxithromycin.

In another embodiment, the invention provides a pharmaceutical composition comprising an effective amount of doxycycline and roxithromycin.

In various embodiments, the pharmaceutical compositions of the present application further comprise vitamin D and/or fish oil and/or cod liver oil and/or other sources of DHA and EPA including but not limited to Krill oil. In other embodiments, the present application further comprise N-acetyl cysteine (NAC). In other embodiments, the pharmaceutical compositions of the present application further comprise Augmentin and/or Diamox and/or Rifater.

In another aspect, the invention provides a kit comprising two tablets or capsules wherein a first tablet or capsule comprises a combination of roxithromycin and minocycline and wherein a second tablet or capsule comprises fish oil and/or cod liver oil and/or other sources of EPA and DHA such as, but not limited to, Krill oil.

In another aspect, the invention provides a kit comprising two tablets or capsules wherein a first tablet or capsule comprises a combination of roxithromycin and minocycline and wherein a second tablet or capsule comprises vitamin D.

In another aspect, the invention includes a kit comprising three tablets or capsules wherein a first tablet or capsule comprises a combination of roxithromycin and minocycline, and wherein a second tablet or capsule comprises fish oil and/or cod liver oil and/or other sources of EPA and DHA such as, but not limited to, Krill oil. and wherein a third tablet or capsule comprises vitamin D.

In various embodiments, the kits of the present invention may further comprise Augmentin and/or Diamox and/or Rifater and/or N-acetyl cysteine (NAC).

The details of the invention are set forth in the accompanying description below.

Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs.

DETAILED DESCRIPTION OF THE INVENTION

The present invention is based, in part, on the discovery that administration of an effective amount of a macrolide and an effective amount of a tetracycline can treat various diseases associated with inflammation and/or accelerated aging.

In one aspect, the invention includes a method of treating a disease associated with inflammation and/or accelerated aging, the method comprising administering an effective amount of a macrolide and an effective amount of a tetracycline to a patient in need thereof.

In some embodiments, the invention includes a method of treating a disease associated with inflammation and/or accelerated aging, the method comprising administering an effective amount of a macrolide, wherein the macrolide is selected from the group consisting of clarithromycin and roxithromycin and an effective amount of a tetracycline, wherein the tetracycline is minocycline or doxycycline to a patient in need thereof.

In various embodiments, the methods of the present invention further comprise instances in which the macrolide has both anti-infective and anti-inflammatory properties.

In some embodiments, the methods of the present invention comprise a macrolide that is selected from: ansamycin, azalide, azithromycin, boromycin, brefeldin A, candicidin, carbomycin A, cethromycin, clarithromycin, dirithromycin, erythromycin, fidaxomicin, filipin, flurithromycin, kitasamycin, macrocin, mepartricin, midecamycin, midecamycin acetate, miocamycin, nargenicin, oleandomycin, oligomycin, pentamycin, pikromycin, pristinamycin IIA, rokitamycin, roxithromycin, solithromycin, spiramycin, streptogramin A, streptovaricin, telithromycin, telithromycin, troleandomycin, troleandomycin, tulathromycin, tylocine, tylosin, tylosin/tylocine, and virginiamycin S1. In some embodiments, the macrolide is selected from clarithromycin and roxithromycin.

In some embodiments, the methods of the present invention comprise a tetracycline that is selected from: chlortetracycline, demeclocycline, doxycycline, lymecycline, meclocycline, methacycline, minocycline, oxytetracycline, rolitetracycline, tetracycline, and tigecycline. In some embodiments, the tetracycline is minocycline.

In some embodiments, the methods of the present invention further comprise a step of administering an effective amount of an immunomodulating agent. In some embodiments, the immunomodulating agent is vitamin D. In some embodiments, the effective amount of vitamin D is sufficient to ensure adequate blood levels of 25-hydroxy vitamin D. In some embodiments, the adequate blood level of 25-hydroxy vitamin D is about 40-100 ng/ml. In various embodiments, the methods of the present invention further comprise administering an effective amount of cod liver oil and/or an effective amount of fish oil and/or other sources of EPA and DHA such as, but not limited to, Krill oil.

In some embodiments, the methods of the present invention further comprise a step of administering an effective amount of cod liver oil and/or fish oil. In some embodiments, the methods of the present invention further comprise a selection of cod liver oil over fish oil which is determined by the presence of fat soluble vitamins A and D. In some embodiments, the methods of the present invention further comprise a selection of fish oil over cod liver oil which is determined by the presence of vitamin A at a level of up to about 4,000 IU/kg of body weight.

In some embodiments, the cod liver oil and fish oil are administered daily, at a dose of about 15 grams/day such that the ratio of omega-6-polyunsaturated fatty acids to omega-3-polyunsaturated fatty acids is about 4:1 or less, about 5:1 or less, or about 6:1 or less.

In some embodiments, the cod liver oil is administered before the fish oil. In some embodiments, the fish oil is administered before the cod liver oil. In some embodiments, the cod liver oil and fish oil are simultaneously administered.

In some embodiments, the methods of the present invention further comprise a step of administering an effective amount of a source of natural EPA and DHA.

In some embodiments, the methods of the present invention further comprise a step of administering an effective amount of amoxicillin and a β-lactamase inhibitor. In some embodiments, the β-lactamase inhibitor is clavulanate potassium. In some embodiments, the combination is Augmentin.

In some embodiments, the methods of the present invention further comprise a step of administering an effective amount of a carbonic anhydrase inhibitor. In some embodiments, the carbonic anhydrase inhibitor is acetazolamide. In some embodiments, the acetazolamide is Diamox. In other embodiments, the method further comprises the administering an effective amount of a additional agent comprising Rifampin. In other embodiments, the method further comprises the administering an effective amount of an additional agent comprising isoniazid. In still other embodiments, the method further comprises administering of an effective amount of an additional agent comprising pyrazinamide. In various embodiments, the additional agent is Rifater. In still other embodiments, the method further comprises administering of an effective amount of an additional agent comprising N-acetyl cysteine (NAC).

In some embodiments, the methods of the present invention further comprise the administering an effective amount of a lithium agent. In some embodiments, the lithium agent is a lithium salt. In further embodiments, the lithium agent is a neuroprotective agent. In some embodiments, the lithium agent is used at a dose of less than about 50 mg, less than about 25 mg, less than about 10 mg, or less than about 5 mg.

In still further embodiments, the methods of the present invention are directed at a disease selected from: Addison's disease; ALS (Lou Gehrig's Disease); Alzheimer's disease; amyloidosis; angina; rheumatoid arthritis; arthritis; asthma; atherosclerosis; auto immune disease; bronchiectasis; cancer; cardiac arrythmias; cardiac failure; cardiomyopathy; cardiovascular diseases; chronic fatigue syndrome; chronic obstructive pulmonary disorder; chronic renal disease; coronary artery disease; Crohn's disease; dementia(s); diabetes (II); diabetes insipidus; diabetes mellitus type 1, diabetes mellitus type 2; diseases of infections; diseases of inflammation/inflammatory disorders; diseases of intracellular infections; diseases of obligate intracellular infections, dysrhythmias; endocarditis; epilepsy; fungal diseases; giant cell arteritis; glaucoma; haemophilia; heart failure; hyperhomocysteinemia; hyperlipidaemia; hypertension; hypothyroidism; inclusion body myotosis; leukocyte defects; Lewy body dementia; lipid imbalance (Total Cholesterol: HDL is about 3:1 or, preferably, less); lupus; Lyme disease; multiple sclerosis; myopathies; neurological and/or neurodegenerative diseases; neuromuscular diseases; Parkinson's disease; peripheral vascular disease; polymyalgia rheumatica; rheumatoid arthritis; schizophrenia; systemic lupus erythematosus; taupathies; ulcerative colitis; vasculitis; viral diseases and Whipple's disease.

In a specific embodiment, the disease is a neurological and/or neurodegenerative disease and/or cardiovascular disease. In another specific embodiment, the disease is dementia. In another specific embodiment, the disease is early cognitive impairment. In yet another specific embodiment, the disease is macular degeneration. In still another specific embodiment, the disease is Alzheimer's disease. In a specific embodiment, the disease is and/or presents nuclear cataracts. In another specific embodiment, the disease is and/or presents cortical cataracts. In yet another specific embodiment, the disease is stem cell disease. In still another specific embodiment, the disease is associated with an unfolded or misfolded protein response. In a specific embodiment, the disease is retinitis pigmentosa. In a further specific embodiment, the disease is cystoid macular edema. In a further specific embodiment, the disease is glaucoma, various diseases of the nerve fiber layer, various diseases of the retina, various diseases of the lens, various diseases of the cornea, or various diseases of the fluids of the eye.

In specific embodiments, the cardiovascular disease is selected from the group consisting of arterial disease, atheroma, atherosclerosis, arteriosclerosis, atrial fibrillation, coronary artery disease, arrhythmia, angina pectoris, congestive heart disease, myocardial infarction, stroke, transient ischemic attack (TIA), aortic aneurysm, cardiopericarditis, infection of the heart, inflammation of the heart, valvular disorders, vascular disorders, and clotting disorders.

In some embodiments, the methods of the present invention further comprise a patient which comprises a bacterial infection.

In specific embodiments, the bacteria is selected from: *Abiotrophia, Acetivibrio, Acholeplasma, Achromobacter, Acidaminococcus, Acidovorax, Acinetobacter, Actinobacillus, Actinobaculum, Actinomadura, Actinomyces, Aegyptianella, Aerococcus, Aeromonas, Afipia, Alcaligenes, Alloiococcus, Allomonas, Alteromonas, Amycolata, Anaerobiospirillum, Anaerorhabdus, Anaplasma, Arachnia, Arcanobacterium, Arcobacter, Arizona, Arsenophonus, Arthrobacter, Atopobium, Bacillus, Bacteroides, Balneatrix, Bartonella, Beneckea, Bergeyella, Bifidobacterium, Bilophila, Bordetella, Borrelia, Brachyspira, Brevibacterium, Brevinema, Brevundimonas, Brucella, Burkholderia, Calymmatobacterium, Campylobacter, Capnocytophaga, Cardiobacterum, Carnobacterium, Catonella, Cedecea, Cellulomonas, Centipeda, Chlamydia, Chlamydophila, Chromobacterium, Chryseobacterium, Citrobacter, Clavibacter, Clostridium, Comamonas, Corynebacterium, Cowdria, Coxiella, Curtobacterium, Cytophaga, Dermatiphulus, Dermatophilus, Dialister, Dichelobacter, Dolosigranulum, Edwardsiella, Ehrlichia, Eikenella, Empedobacter, Enterobacter, Enterococcus, Eperythrozoon, Erlichia, Erwinia, Erysipelothrix, Escherichia, Eubacterium, Eurbacterium, Ewingella, Facklamia, Faenia, Falcivibrio, Flavobacterium, Flexibacter, Fluoribacter, Francisella, Fusobacterium, Gardnerella, Gemella, Globicatella, Gordonia, Haemobartonella, Haemophilus, Hafnia, Hallella, Hartmanella, Helcococcus, Helicobacter, Herellea, Johnsonella, Jonesia, Kingella, Klebsiella, Kluyvera, Koserella, Lactobacillus, Lactococcus, Lawsonia, Leclercia, Legionella, Leptospira, Levinea, Liberobacter, Listeria, Listonella, Mannheimia, Megasphaera, Melissococcus, Microvirgula, Mima, Mitsuokella, Mobiluncus, Moraxella, Moraxella (Branhamella), Morganella, Morococcus, Mycobacterium, Mycoplasma, Myroides, Neisseria, Neorickettsia, neurolyticum, Nocardia, Nocardiopsis, Nocarida, Ochrobactrum, Oligella, Orienta, Ornithobacterium, Paenibacillus, Pantoea, Pasteurella, Peptococcus, Peptostreptococcus, Photobacterium, Piscirickettsia, Plesiomonas, Porphyromonas, Prevotella, Propionibacterium, Proteus, Providencia, Pseudoalteromonas, Pseudomonas, Pseudoramibacter, Psychrobacter, Ralstonia, Renibacterium, Rhodococcus, Rickettsia, Riemerella, Rochalimaea, Saccharopolyspora, Salmonella, Sanguibacter, Selenomonas, Serpulina, Serratia, Serretia, Shewanella, Shigella, Sphaerophorus, Sphingobacterium, Sphingomonas, Spiroplasma, Sporichthya, Staphylococcus, Stenotrophomonas, Streptobacillus, Streptococcus, Streptomyces, Sutterella, Suttonella, Tatlockia, Tatumella, Taylorella, Tissierella, Treponema, Treponema pallidum, Tsukamurella, tubercle bacillus, Turicella, Ureaplasma, Vagococcus, Veillonella, Vibrio, Waddlia, Xanthomonas, Xylella, Xylophilus,* and *Yersinia*.

In some embodiments, the methods of the present invention further comprise a patient which comprises a viral infection.

In specific embodiments, the virus is selected from: Adenoviridae, Arenaviridae, Astroviridae, Baculoviridae, Birnaviridae, Bornaviridae, Bunyaviridae, Caliciviridae, Circoviridae, Coronaviridae, Filoviridae, Flaviviridae, Hepadnaviridae, Herpesviridae, Iridoviridae, Orthomyxoviridae, Papovaviridae, Paramyxoviridae, Parvoviridae, Picornaviridae, Poxviridae, Prion, Reoviridae, Retroviridae, Rhabdoviridae, Rubella, Togaviridae, and Toroviridae.

In some embodiments, the methods of the present invention further comprise a patient which comprises a protozoan infection.

In some embodiments, the methods of the present invention further comprise a patient which comprises a fungal infection.

In specific embodiments, the fungus is selected from: *Absidia, Acremonium, Ajellomyces, Aphanomyces, Arthroderma, Aspergillus, Basidiobolus, Blastomyces, Candida, Capronia, Ceratocystis, Cladophialophora, Cladosporium, Coccidioides, Cryptococcus, Dactylaria, Dermatophilus, Emmonsia, Emmonsiella, Epidermophyton, Exophiala, Filobasidiella, Fonsecaea, Fusarium, Geotrichum, Giberrella, Histoplasma, Hortea, Leptosphaeria, Loboa, Madurella, Microsporum, Monosporium, Mucor, Nannizzia, Nectria, Neotestudina, Ochroconis, Ophiostoma, Paecilomyces, Paracoccidioides, Penicillium, Phialophora, Phytophthora, Pierre, Pseudallescheria, Rhamichlorium, Rhinocladiella, Rhinosporidium, Rhizopus, Scedosporium, Sporothrix, Stachybotrys, Trichophyton, Trichosporon, Xylohypha*, and *Zymomema*.

In some embodiments, the methods of the present invention further comprise a patient which comprises an infection selected from: toxoplasmosis, *Chlamydophila pneumoniae*, Lyme disease, Q-fever, *Rickettsia*(s), *Mycoplasma*(s), eubacterial infection, *H. pylori, S. aureus*, Chlamydia, and enterobacteriaceae.

In some embodiments, the methods of the present invention further comprise a patient which comprises an inflammation of unknown origin, an immune-mediated disease, or an auto-immune disease affecting the eye. In specific embodiments, an auto-immune disease affecting the eye includes Sarcoidosis, Vogt-Koyanagi-Harada syndrome, Birdshot retinochoriodopathy, and Behcet's disease. In still other embodiments, the methods of the present invention further comprise a patient which comprises chronic uveitis.

In one embodiment, the methods of the present invention comprise a patient wherein the patient comprises a parasite. In specific embodiments, the parasite is selected from: *Acanthamoeba, Ancylostoma, Ancylstoma, Angiostrongylus, Anisakis, Ascaris, Babesia, Balantidium, Blastocystis, Brugia, Capillaria, Clonorchis, Coccidia, Cochliomyia, Contracaecum, Cryptosporidium, Custocercis, Cyclospora, Cysticercus, Dicrocoelium, Dientamoeba, Dipetalonema, Diphyllobothrium, Dipylidium, Dracunculus, Echinococcus, Eimeria, Encephalitozoon, Entamoeba, Enterobius, Enterocytozoon, Fasciola, Fasciolopsis, Giardia, Gnathostoma, Gongylonema, Haemonchus, Heterophyes, Hymenolepis, Isopora, Leishmania, Loa, Mansonella, Metagonimus, Microsporidium, Naegleria, Necator, Oesophagostomum, Onchocerca, Opisthorchis, Paragonimus, Piroplasma, Plasmodium, Pneumocystis, Pseudoterranova, Sarcocystis, Schistosoma, Strongyloides, Taenia, Ternidens Theileria, Toxocara, Toxoplasma, Trichinella, Trichomonas, Trichostrongylus, Trichuris, Trypanosoma, Varroa*, and *Wuchereria*.

In some embodiments, the methods of the present invention further comprise elevating the HDL cholesterol level in the patient such that a ratio of total cholesterol to HDL is reduced. In specific embodiments, the HDL cholesterol level is raised such that the ratio of total cholesterol to HDL is about 3:1, about 2:1 or about 1:1.

In some embodiments, the methods of the present invention further comprise the patient's HDL cholesterol level being increased by administering an effective amount of (a) macrolide; (b) tetracycline; and (c) vitamin D, wherein said macrolide, tetracycline and vitamin D may be administered either in any order or concurrently. In a specific embodiment, the order of administration is (1) macrolide; (2) tetracycline; and (3) vitamin D. In a specific embodiment, Augmentin and/or Diamox and/or Rifater is also administered. In a further specific embodiment, the order of administration is (1) macrolide; (2) tetracycline; (3) Augmentin and/or Diamox and/or Rifater, and/or N-acetyl cysteine (NAC) and (4) vitamin D.

In some embodiments, the methods of the present invention further comprise the patient's HDL cholesterol level being increased by administering an effective amount of (a) macrolide; (b) tetracycline; and (c) cod liver oil, wherein said macrolide, tetracycline and cod liver oil may be administered either in any order or concurrently. In a specific embodiment, Augmentin and/or Diamox and/or Rifater is also administered. In a specific embodiment, the order of administration is (1) macrolide; (2) tetracycline; and (3) cod liver oil. In a further specific embodiment, the order of administration is (1) macrolide; (2) tetracycline; (3) Augmentin and/or Diamox and/or Rifater, and/or N-acetyl cysteine (NAC), and (4) cod liver oil.

In some embodiments, the methods of the present invention further comprise the patient's HDL cholesterol level being increased by administering an effective amount of (a) macrolide; (b) tetracycline; (c) vitamin D; and (d) cod liver oil, wherein said macrolide, tetracycline, vitamin D, and cod liver oil may be administered either in any order or concurrently. In a specific embodiment, Augmentin and/or Diamox and/or Rifater and/or N-acetyl cysteine (NAC) is also administered. In another specific embodiment, the order of administration is (1) macrolide; (2) tetracycline; (3) vitamin D; and (4) cod liver oil. In a further specific embodiment, the order of administration is (1) macrolide; (2) tetracycline; (3) Augmentin and/or Diamox and/or Rifater and/or N-acetyl cysteine (NAC); (4) vitamin D; and (5) cod liver oil.

In some embodiments, the methods of the present invention further comprise the patient's inflammation being reduced by administering an effective amount of (a) macrolide; (b) tetracycline; (c) vitamin D; and (d) cod liver oil, wherein said macrolide, tetracycline, vitamin D, and cod liver oil may be administered either in any order or concurrently. In a specific embodiment, Augmentin and/or Diamox and/or Rifater and/or N-acetyl cysteine (NAC) is also administered. In another specific embodiment, the order of administration is (1) macrolide; (2) tetracycline; (3) vitamin D; and (4) cod liver oil. In a further specific embodiment, the order of administration is (1) macrolide; (2) tetracycline; (3) Augmentin and/or Diamox and/or Rifater and/or N-acetyl cysteine (NAC); (4) vitamin D; and (5) cod liver oil.

In some embodiments, the compositions of the present invention are administered for up to 1 month, up to 2 months, up to 3 months, up to 4 months, up to 5 months, up to 6 months, up to 7 months, up to 8 months, up to 9 months, up to 10 months, up to 11 months, and up to 12 months. In further embodiments, the compositions of the present invention are administered for up to 1 year, up to 1.25 years, up to 1.5 years, up to 1.75 years, up to 2 years, up to 2.5 years, up to 3 years, up to 4 years, up to 5 years, up to 7.5 years, up to 10 years, or up to 15 years. In further embodiments, the compositions of the present invention are administered for the patient's lifetime.

In some embodiments, the compositions of the present invention are administered in a dosage that is below the normal standard of care administrated to a subject (e.g. subclinical dosing; see, e.g., L S Goodman, Gilman, A. *The Pharmacological Basis of Therapeutics,* 5th ed.; MacMillan: New York, 1975, pp. 201-226).

In various embodiments, the methods provide for administering the macrolide and tetracycline together. In various embodiments, the methods provide for administering the macrolide and tetracycline sequentially.

In various embodiments, the methods provide for administering the macrolide, tetracycline, and vitamin D together. In various embodiments, the methods provide for administering the macrolide, tetracycline, and vitamin D sequentially.

In various embodiments, the methods provide for administering the macrolide, tetracycline, and cod liver oil together. In various embodiments, the methods provide for administering the macrolide, tetracycline, and cod liver oil sequentially.

In another aspect, the invention includes a pharmaceutical composition comprising an effective amount of a macrolide and an effective amount of a tetracycline.

In another aspect, the invention includes a pharmaceutical composition comprising an effective amount of minocycline and clarithromycin.

In another aspect, the invention includes a pharmaceutical composition comprising an effective amount of minocycline and roxithromycin.

In various aspects, the inventive pharmaceutical compositions also comprise an effective amount of Augmentin and/or Diamox and/or Rifater and/or N-acetyl cysteine (NAC).

In some embodiments, the pharmaceutical compositions further comprise excipients. In some embodiments, the pharmaceutical compositions further comprise single or multiple unit capsules. In some embodiments, the pharmaceutical compositions further comprise single or multiple unit tablets. In some embodiments, the pharmaceutical compositions further comprise single or multiple unit suspensions. In some embodiments, the pharmaceutical compositions further comprise single or multiple unit emulsions. In some embodiments, the pharmaceutical compositions further comprise active ingredients that are mixed together in a tablet. In some embodiments, the pharmaceutical compositions further comprise active ingredients that are partitioned. In some embodiments, the pharmaceutical compositions are formulated for oral administration. In some embodiments, the pharmaceutical compositions are hard gelatin capsules. In some embodiments, the pharmaceutical compositions are soft gelatin capsules.

In another aspect, the invention includes a kit comprising two tablets or capsules wherein a first tablet or capsule comprises a combination of roxithromycin and minocycline and wherein a second tablet or capsule comprises cod liver oil.

In another aspect, the invention includes a kit comprising two tablets or capsules wherein a first tablet or capsule comprises a combination of roxithromycin and minocycline and wherein a second tablet or capsule comprises vitamin D.

In another aspect, the invention includes a kit comprising three tablets or capsules wherein a first tablet or capsule comprises a combination of roxithromycin and minocycline and wherein a second tablet or capsule comprises cod liver oil and wherein a third tablet or capsule comprises vitamin D.

In another aspect, the invention includes a kit comprising three tablets or capsules wherein a first tablet or capsule comprises roxithromycin and wherein a second tablet or capsule comprises minocycline, and wherein a third tablet or capsule comprises cod liver oil.

In another aspect, the invention includes a kit comprising four tablets or capsules wherein a first tablet or capsule comprises roxithromycin and wherein a second tablet or capsule comprises minocycline, wherein a third tablet or capsule comprises cod liver oil, and wherein a fourth tablet or capsule comprises vitamin D.

In various aspects, the inventive kits also comprise an effective amount of Augmentin and/or Diamox and/or Rifater and/or N-acetyl cysteine (NAC).

In a specific embodiment, the kits further comprise blister packages.

DEFINITIONS

The articles "a" and "an" are used in this disclosure to refer to one or more than one (i.e., to at least one) of the grammatical object of the article. By way of example, "an element" means one element or more than one element.

The term "and/or" is used in this disclosure to mean either "and" or "or" unless indicated otherwise.

A "subject" is a mammal, e.g., a human, mouse, rat, guinea pig, dog, cat, horse, cow, pig, or non-human primate, such as, but not limited to, a monkey, chimpanzee, baboon or rhesus, and the terms "subject" and "patient" are used interchangeably herein.

Representative "pharmaceutically acceptable salts" include, e.g., water-soluble and water-insoluble salts, such as, but not limited to, the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, magnesium, malate, maleate, mandelate, mesylate, methylbromide, methylnitrate, methylsulfate, mucate, napsylate, nitrate, Nmethylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, ptoluenesulfonate, salicylate, stearate, subacetate, succinate, sulfate, sulfosalicylate, suramate, tannate, tartrate, teoclate, tosylate, triethiodide and valerate salts.

An "effective amount" is an amount effective for treating or preventing a disease.

The term "carrier" encompasses carriers, excipients, and diluents and means a material, composition or vehicle, such as, but not limited to, a liquid or solid filler, diluent, excipient, solvent or encapsulating material, involved in carrying or transporting a pharmaceutical agent from one organ, or portion of the body, to another organ, or portion of the body.

The term "treating," with regard to a subject, refers to improving at least one symptom of the subject's disorder. Treating can be curing, improving, or at least partially ameliorating the disorder.

The term "disorder" is used in this disclosure to mean, and is used interchangeably with, the terms disease, condition, or illness, unless otherwise indicated.

The term "administer," "administering," or "administration" as used in this disclosure refers to either directly administering a compound or pharmaceutically acceptable salt of the compound or a composition to a subject, or administering a prodrug derivative or analog of the compound or pharmaceutically acceptable salt of the compound or composition to the subject, which can form an equivalent amount of active compound within the subject's body.

The term "prodrug," as used in this disclosure, means a compound which is convertible in vivo by metabolic means (e.g., by hydrolysis) to a composition of this application.

Chronic Inflammation and Diseases of Aging

Chronic systemic inflammation often presents in parallel with the major diseases of aging. Thus, chronic systemic inflammation is a strong marker, and often indicated as a cause, of many seemingly unrelated, age-related diseases. As humans grow older, the processes resulting from systemic inflammation or its causes can inflict devastating degenerative effects throughout the body. T P Shanley, et al. "The role of cytokines and adhesion molecules in the development of inflammatory injury." Mol Med Today. 1995 April; 1(1): 40-5; M F McCarty "Interleukin-6 as a central mediator of cardiovascular risk associated with chronic inflammation, smoking, diabetes, and visceral obesity: down-regulation with essential fatty acids, ethanol and pentoxifylline." Medical Hypotheses, Volume 52, Issue 5, Pages 465-477 (May 1999); S A Brod "Unregulated inflammation shortens human functional longevity." Inflammation Research. Volume 49, Number 11, 561-570. The pathological consequences of inflammation are discussed in the medical literature. Persuasive scientific evidence exists that correcting a chronic inflammatory disorder, preferably at the root-cause, will enable many of the infirmities of aging to be delayed, prevented, or reversed.

Chronic inflammation presents in atherosclerosis and is also involved in diseases as diverse as cancer, heart valve dysfunction, obesity, diabetes, congestive heart failure, digestive system diseases, Alzheimer's disease, Parkinson's disease, neurological and/or neurodegenerative diseases and general dementias, among others. Nemat Khansari, et al. "Chronic Inflammation and Oxidative Stress as a Major Cause of Age-Related Diseases and Cancer." Recent Patents on Inflammation & Allergy Drug Discovery 2009, 3, 73-80.

Aging can result in an increase of inflammatory cytokines (and other destructive cell-signaling chemicals) that contribute to the progression of many degenerative diseases. Rheumatoid arthritis is a classic autoimmune disorder in which excess levels of cytokines such as, but not limited to, tumor necrosis factor-alpha (TNF-a), interleukin-6 (IL-6), interleukin 1b (IL-1 (b), and/or interleukin-8 (IL-8) are known to cause or contribute to the inflammatory syndrome.

In aged people with multiple degenerative diseases, the inflammatory marker, C-reactive protein, is often sharply elevated, indicating the presence of an underlying inflammatory disorder. P M Ridker and J D Silvertown "Inflammation, C-Reactive Protein, and Atherothrombosis." Journal of Periodontology. August 2008, Vol. 79, No. 8, Pages 1544-1551. When a cytokine blood profile is conducted on people in a weakened condition, an excess level of one or more of the inflammatory cytokines, e.g., TNF-a, IL-6, IL-1(b), or IL-8, may be found.

One potential marker of and component of accelerated aging and disease processes is homocysteine. Hyperhomocysteinemia is a risk factor for inflammatory diseases including cardiovascular disease, stroke, renal failure and cancer. Hyperhomocysteinemia not only is produced from inflammation, but also the oxidative stress generated from hyperhomocysteinemia promotes inflammation. As a result, elevated homocysteine and inflammation markers may occur at the same time, and may be correlated with each other. Because of their different inflammatory pathways, the simultaneous presence of homocysteine and inflammation markers corroborates a chronic disease process.

Connection Between Cardiovascular Disease (CVD) and Neurodegnerative Diseases

Alzheimer's disease (AD) is a progressive age-related neurodegenerative disorder that is the most common form of dementia affecting people 65 years and older. The pathologic features of AD are the presence of senile plaques (SPs) and neurofibrillary tangles (NFTs) in the brain. SPs are extracellular beta amyloid protein (A beta) deposits derived from amyloid precursor protein (APP) while NFTs are intraneuronal structures composed of tau protein. Clinically, AD is characterized by impairment in memory, visuospatial skills, complex cognition, language, emotion and personality. Although the exact cause of AD remains elusive, mounting evidence continues to support the involvement of inflammation in the development of AD.

Inflammation was first implicated in AD pathology in the 1990s with the neuropathological findings of activated inflammatory cells surrounding the amyloid plaques. P L McGeer and E G McGeer, "The inflammatory system of brain: implications for therapy of Alzheimer and other neurodegenerative disorders." Brain Res. Rev. (1995) 21, 195-218.

Clinical symptoms of dementia relate to the affected areas of the brain. In AD the symptoms are caused by a progressive loss of cholinergic function due to neuronal cell death in the hippocampus and cerebral cortex, brain regions involved in thought processing and memory. At the microscopic level, the core hallmarks of AD consist of two kinds of protein aggregates, amyloid plaques and hyper-phosphorylated tangles of tau-protein. Amyloid precursor protein (APP) is a trans-membrane protein formerly without known function that is constitutively cleaved into peptides during cell metabolism. The amyloidogenic 40 and 42 amino acid (A beta) peptide is released after cleavage by beta-secretase and gamma-secretase enzymes and is usually quickly removed from the brain. However, in the case of overproduction or impaired clearance, A beta aggregates into extracellular oligomers, fibrils and eventually, plaques. Tau is an intracellular microtubule binding protein that, when hyperphosphorylated, will cause disassembly of microtubules and thus will impair axonal transport and compromise neuronal and synaptic function. Whether tangle formation is a cause or a consequence of the disease is still under debate.

The dominating hypothesis for the cause of AD is the amyloid cascade hypothesis. J A Hardy and G A Higgins. "Alzheimer's disease: the amyloid cascade hypothesis." Science 1992; 256(5054): 184-185. According to this hypothesis, abnormal metabolism of the amyloid precursor protein (APP) and the subsequent accumulation of toxic A beta peptides are key events in AD pathology. Accumulated A beta is thought to lead to neuronal degeneration and functional loss via toxic effects and down-stream events including tangle formation, oxidative stress and chronic inflammation. Support for a central role of A beta in AD pathology includes the finding that the mutations implicated in familial AD are present in genes related to A beta production. So far, several mutations have been found in APP and in the genes encoding for the enzymatic center of the gamma-secretase complex, presenilin 1 and presenilin.

Although there is a substantial body of evidence in support of the amyloid hypothesis, the triggers of amyloid aggregation in sporadic cases of AD are still not understood. Most importantly, there are no commonly known means to alter or manipulate the amyloid cascade for a more favorable prognosis.

Recently, an alternative view regarding the function of the A beta protein has emerged. A beta has been shown to be a ligand for a number of different receptors and other molecules, transported by complex trafficking pathways between tissues and across the blood brain barrier, modulated in response to a variety of environmental stressors, and able to induce pro-inflammatory activities. Despite these clues, the normal physiological role of A beta remains unknown.

Inflammation and Other Diseases
Neurological and/or Neurodegenerative Diseases and Inflammation Inflammation of the central nervous system (CNS) (neuroinflammation) is now recognized to be a feature of many neurological disorders. E E Tuppo and H R Arias "The Role of Inflammation in Alzheimer's Disease." The International Journal of Biochemistry & Cell Biology 37 (2005) 289-305. In multiple sclerosis, there is prominent infiltration of various leukocyte subsets into the CNS. In Parkinson's disease and Alzheimer's disease, there is intense activation of microglia with resultant elevation of many inflammatory mediators within the CNS. An extensive dataset describes neuroinflammation to have detrimental consequences, but results emerging largely over the past decade have indicated that aspects of the inflammatory response are beneficial for CNS outcomes.

Benefits of neuroinflammation now include neuroprotection, the mobilization of neural precursors for repair, remyelination, and even axonal regeneration. The findings that neuroinflammation can be beneficial should not be surprising, as a properly directed inflammatory response in other tissues is a natural healing process after an insult. Thus, there is a potential dual aspect of neuroinflammation in being a hindrance on the one hand but also a significant help for recovery of the CNS on the other.

Inflammation is the body's response to infections and tissue injury. C Gabay and I Kushner. "Acute-Phase Proteins and Other Systemic Responses to Inflammation." N Engl J Med 1999; 340(6): 448-454. The inflammatory response is orchestrated by the cells of the immune system, both from the "adaptive" branch (including T-cells and B-cells with the capacity to induce long-term memory of encountered pathogens, "immunization") and the "innate" branch (including monocytes, macrophages, dendritic cells, and mast cells, etc., that are targeted against common pathogen antigens).

Inflammation was first implicated in the development of AD in the beginning of the 1990s when key discoveries were made. The first discovery was that immune competent cells (activated microglia and astrocytes) and inflammatory proteins (e.g. cytokines and complement) are found in the vicinity of the amyloid plaques and the neurofibrillary tangles. P S Aisen and K L Davis "Inflammatory mechanisms in Alzheimer's disease: implications for therapy." Am J Psychiatry 1994; 151(8): 1105-1113. Many of the earliest results were at first dismissed as inaccurate given the perception of the brain as an "immune privileged" organ, i.e. an organ that does not elicit inflammation in response to antigens or damage. However, there is now abundant literature on the presence of acute phase proteins in amyloid plaques, activated microglial cells that stain for inflammatory cytokines, and components of the complement system in brain tissue of AD patients.

Since the initial discovery of a potential inflammatory component to AD, studies have diversified to look at a multitude of inflammation-associated risk factors for cognitive function, cognitive decline, AD, dementia and progression in dementia; including circulating inflammatory markers, cerebral spinal fluid (CSF) markers of inflammation, genetic sequence variation in immune-related genes, and proxies of inflammatory load (e.g. gingivitis) and allotropic factors. R Schmidt, et al. "Early inflammation and dementia: a 25-year follow-up of the Honolulu-Asia Aging Study." Ann Neurol 2002; 52(2): 168-174. The mechanisms by which peripheral inflammation could affect AD development are not known but are hypothesized to be either contributors to neuronal degeneration and/or factors that lower the clinical threshold for dementia. The brain has traditionally been viewed as an immune-privileged organ since the normal immunological surveillance of the immune system does not pass over the brain. However, it is now clear that blood borne cytokines can cross the blood-brain barrier (BBB) at specific sites and when the BBB is damaged there are neuro-immune interactions. In regards to circulating markers of inflammation, some studies have interpreted elevated blood levels as a spill-over from ongoing inflammation in the brain.

An interesting development during the last decade is that traditional risk factors of cardiovascular disease also have been linked to AD. High blood pressure (BP), elevated cholesterol levels, obesity, smoking, diabetes, and atherosclerosis have been associated with AD. Similarly, exercise has been associated with reduced risk. E B Larson "Physical activity for older adults at risk for Alzheimer disease." JAMA 2008; 300(9): 1077-1079. It is possible that low-grade systemic inflammation constitutes a common denominator in neurological and/or neurodegenerative and vascular diseases, possibly via detrimental effects on the vasculature, leading to a dysfunctional BBB and inflammatory stimuli of the brain. The mechanisms of action and thus treatments for neurological and/or neurodegenerative diseases thus intersect with those for cardiovascular diseases.

Cardiovascular disease (CVD) and risk factors for CVD have been linked to cognitive impairment and dementia. A B Newman, et al. "Dementia and Alzheimer's disease incidence in relationship to cardiovascular disease in the Cardiovascular Health Study cohort." J Am Geriatr Soc 2005; 53(7): 1101-1107. CVD is a well established risk factor for vascular dementia (VaD) but the association with AD is unclear. The main underlying cause of CVD is atherosclerosis. Atherosclerosis is an inflammatory disease of the blood vessels that eventually can lead to vessel rupture or thrombosis. If this occurs in the cerebral blood vessels (stroke) or the coronary arteries (myocardial infarction), it can be deadly. It has been hypothesized that atherosclerosis-induced brain hypoperfusion, oxidative stress, and/or inflammation could contribute directly to the development of the neuropathology in Alzheimer's disease. I Casserly and E Topol. "Convergence of artherosclerosis and Alzheimer's disease; inflammation, cholesterol, and misfolded proteins." Lancet 2004; 363(9415): 1139-1146. The connection between A beta and microbes and CVD and pathogens implies that AD as well as vascular dementias has a common mechanistic root including all the complexities of hypoxia and other causes of cell and membrane dysfunction discussed here.

Reviews of epidemiological studies conclude that there appears to be an association between CVD and risk factors for CVD with AD but the nature of the association remains unknown. Newman A B, et al. "Dementia and Alzheimer's disease incidence in relationship to cardiovascular disease in the Cardiovascular Health Study cohort." J Am Geriatr Soc 2005; 53(7): 1101-1107. Endothelial and blood-brain barrier function is also known to be impaired in AD, perhaps induced by vascular factors co-existing with AD. An alternative explanation for the association between CVD and AD includes clinical threshold-lower effects on dementia, perhaps as a consequence of subclinical silent infarcts or stroke due to micro-abscess. Consistent with this is a high risk of dementia in immediate conjunction to a CVD event.

It is also likely that there is potential diagnostic bias, prohibiting a, perhaps correct, diagnosis of AD in individuals with CVD. It is thus possible that the contribution of CVD to clinical AD is underestimated.

Another link between CVD and AD has been proposed to be the apolipoprotein E epsilon allele (APOE4). APOE4 is the most well-established genetic risk factor for sporadic AD (with a 3-fold elevated risk for carriers of one allele and up to a 15-fold increased risk for carriers of two alleles compared to the reference level epsilon3/epsilon3) and has also been linked to CVD. However, the role of APOE4 in the association between CVD and AD is unclear. Studies indicate that APOE contributes to AD pathology through direct effects on amyloid beta processing and neurotoxicity and not through enhanced atherosclerosis and cardiovascular disease.

Interleukin-6 (IL6) and C-reactive protein (CRP) are both inflammatory proteins that are secreted upon infection or tissue injury. IL6 is a key regulatory cytokine produced by a variety of cells types including leucocytes, adipocytes and cells of the nervous system. CRP is secreted by the liver and levels increase dramatically upon infection. CRP is therefore measured in clinical practice as an indicator of current infection. CRP and IL6 have been found to be in association with senile plaques and neurofibrillary tangles and to be elevated in temporal cortex in subjects with AD. However, studies of circulating inflammatory markers and genetic variation in inflammatory genes in relation to AD are inconclusive. T Wyss-Coray "Inflammation in Alzheimer disease: driving force, bystander or beneficial response?" Nat Med 2006; 12(9): 1005-1015. Circulating CRP have been shown to predict cardiovascular events in multiple prospective studies but there have been few similar attempts to evaluate associations of inflammatory markers with incident AD and dementia.

Drug Combinations for the Treatment of Neurological and/or Neurodegenerative Diseases Tetracyclines Minocycline is a semi synthetic tetracycline that has been in use for over 30 years. Y Choi et. al. "Minocycline Attenuates Neuronal Cell Death and Improves Cognitive Impairment in Alzheimer's Disease Models." Neuropsychopharmacology (2007) 32, 2393-2404. It is a small (495 Da), highly lipophilic molecule capable of crossing the blood-brain barrier. Minocycline penetrates the cerebral spinal fluid (CSF) of human beings better than doxycycline and other tetracyclines. H MacDonald, et al. "Pharmacokinetic studies on minocycline in man." Clin Pharmacol Ther 1973; 14: 852-61. Minocycline is readily absorbed from the gut after oral ingestion and, because of its low propensity to produce antibiotic resistance; it is commonly used in the management of chronic conditions such as, but not limited to, acne and rosacea. Over 6 million individuals have been treated for acne for an average of 9 months with minocycline with minimal, if any, side effects. V Wee Yong, et al. "The promise of minocycline in neurology." The Lancet Neurology, Vol 3 December 2004 744-750. The frequency of these adverse events is very low, of the order of one in a million individuals treated. Overall, a good safety record for long term clinical use has been established for minocycline. D C Seukeran, et al. "Benefit-risk assessment of acne therapies." Lancet 1997; 349: 1251-52.

In 1998, Yrjanheikki and colleagues showed that minocycline was neuroprotective in an animal model of ischemia. Yrjanheikki et al. "Tetracyclines inhibit microglial activation and are neuroprotective in global brain ischemia." Proc Natl Acad Sci USA 1998; 95: 15769-74. Since then, there have been numerous reports of the efficacy and neuroprotective effects of minocycline in various models of neurological disease, including hemorrhagic and ischemic stroke, multiple sclerosis, spinal-cord injury, Parkinson's disease, Huntington's disease, and amyotrophic lateral sclerosis (ALS).

Many of the beneficial effects of minocycline are demonstrated to be related to an inhibitory activity on inflammation and/or apoptotic cell death, both phenomena being closely associated with neurodegeneration.

Minocycline reduces the proliferation/activation of resting microglial cells and improves cognitive impairment in AD models. Several reports showed that minocycline reduces the expression of inducible nitric oxide synthase and subsequent nitric oxide production as well as caspase-1 activity/expression and thereby prevents the formation of interleukin 1b. Additionally, minocycline can modulate neuronal cell death through an interaction with the apoptotic machinery. Blum D, et al. (2004). "Clinical potential of minocycline for neurodegenerative disorders." Neurobiol Disease 17: 359-366. Minocycline acts at the mitochondria to rescue the collapse of transmembrane potential and the alteration of permeability transition, which are responsible for the cytosolic release of apoptogenic factors such as, but not limited to, cytochrome c, AIF or Smac/Diablo mediating caspase-dependent and independent cell death. Minocycline has been studied recently in in-vitro and in-vivo in AD models. Minocycline attenuates the increases in the phosphorylation that is activation-induced by A beta. V Wee Yong, et al. "The promise of minocycline in neurology." The Lancet Neurology, Vol 3 December 2004 744-750.

Minocycline may also be known as Dynacin, Minocin. Minocin PAC, Myrac, Solodyn, and Vectrin, among others. Further names of these and other agents, can be found by reference to known manuals and websites (see, e.g., *Physicians' Desk Reference*, Medical Economics Co. (65$^{th}$ ed. 2011); United States Pharmacopeia (USP); PubMed Health).

Macrolides

The macrolides, as a class of compounds offer several modes of action important to the treatment of chronic inflammatory disease of the small vessels. In addition to their conventional antimicrobial activity, the macrolide group of antibiotics are known to have a number of anti-inflammatory/immunomodulatory activities, that are emerging as extremely important to patients with chronic inflammatory vascular diseases including Alzheimer's Disease, Parkinson's Disease, Dementia, Macular Degeneration and other neurological and/or neurodegenerative and neuromuscular diseases. These activities involve interactions of the macrolides with the various components of inflammation in patients including proinflammatory mediators, as well as with the microbes themselves.

Inflammation is the final common pathway of various insults, such as, but not limited to, infection, trauma, and allergies to the human body. It is characterized by activation of the immune system with recruitment and activation of inflammatory cells and production of pro-inflammatory mediators. Most inflammatory diseases are characterized by enhanced accumulation of differing proportions of inflammatory cells, including monocytes/macrophages, granulocytes, plasma cells, lymphocytes and platelets. Along with tissue endothelial cells and fibroblasts, these inflammatory cells release a complex array of lipids, growth factors, cytokines and destructive enzymes that cause local tissue damage.

Macrolides include, by way of non-limiting examples, ansamycin, azalide, azithromycin, boromycin, brefeldin A, candicidin, carbomycin A, cethromycin, clarithromycin, dirithromycin, erythromycin, fidaxomicin, filipin, flurithromycin, kitasamycin, macrocin, mepartricin, midecamycin, midecamycin acetate, miocamycin, nargenicin, oleandomycin, oligomycin, pentamycin, pikromycin, pristinamycin IIA, rokitamycin, roxithromycin, solithromycin, spiramycin, streptogramin A, streptovaricin, telithromycin, telithromycin, troleandomycin, tulathromycin, tylocine, tylosin, tylosin/tylocine, and virginiamycin S1. Further names of these and other agents, can be found by reference to known manuals and websites (see, e.g., *Physicians' Desk Reference*, Medical Economics Co. (65$^{th}$ ed. 2011); United States Pharmacopeia (USP); PubMed Health).

Vitamin D

Vitamin D is a group of fat-soluble secosteroids that is an essential vitamin in humans. As used herein vitamin D refers to the various forms of the molecule (non limiting examples are vitamin $D_1$-$D_5$, various pre-vitamins, metabolic products, etc.), analogs, derivatives, and so on. It is useful, inter alia, for the prevention and treatment of defects in the mineralization of cartilage (e.g. rickets), and of bone (e.g. osteomalacia), and even of certain forms of osteoporosis in elderly subjects. It is now accepted that its functions extend well beyond the regulation of bone metabolism and of calcium homeostasis. Among these functions, may include, for example, actions on cell proliferation and differentiation and control of the immune defenses. The discovery of these functions has paved the way for new therapeutic approaches in dermatology, cancerology as well as in the field of autoimmune diseases and that of organ and tissue transplants.

Further names of these and other agents, can be found by reference to known manuals and websites (see, e.g., *Physicians' Desk Reference*, Medical Economics Co. (65$^{th}$ ed. 2011); United States Pharmacopeia (USP); PubMed Health).

Fish Oils and Cod Liver Oil

Fish oils include oil derived from the tissues of oily fish. Fish oils may contain, by way of non-limiting examples, the omega-3 fatty acids eicosapentaenoic acid (EPA) and docosahexaenoic acid (DHA). These molecules are, among others, precursors of eicosanoids that are known to reduce inflammation throughout the body and are thought to have many health benefits.

Further names of these and other agents, can be found by reference to known manuals and websites (see, e.g., *Physicians' Desk Reference*, Medical Economics Co. (65$^{th}$ ed. 2011); United States Pharmacopeia (USP); PubMed Health).

Rifater

Rifater (rifampin, isoniazid and pyrazinamide) is a combination drug containing about 120 mg rifampin, about 50 mg isoniazid, and about 300 mg pyrazinamide for use in antibacterial therapy. The tablets also contain as inactive ingredients such as, but not limited to, povidone, carboxymethylcellulose sodium, calcium stearate, sodium lauryl sulfate, sucrose, talc, acacia, titanium dioxide, kaolin, magnesium carbonate, colloidal silicon dioxide, dried aluminum hydroxide gel, ferric oxide, black iron oxide, carnauba wax, white beeswax, colophony, hard paraffin, lecithin, shellac, and propylene glycol.

Rifampin is a semisynthetic antibiotic derivative of rifamycin. The rifamycins are a group of antibiotics that are synthesized either naturally by the bacterium *Amycolatopsis mediterranei* or artificially. Rifamycins are particularly effective against mycobacteria, and therefore may be used to treat tuberculosis, leprosy, and mycobacterium avium complex (MAC) infections, among others. Without wishing to be bound by theory, the activity of rifamycins may rely on the inhibition of DNA-dependent RNA synthesis, due to the high affinity of rifamycins to prokaryotic RNA polymerase. Rifamycins may include, but are not limited to, rifampicin or rifampin, rifabutin, rifapentine, and rifaximin. Rifampin is a red-brown crystalline powder which is very slightly soluble in water at neutral pH, freely soluble in chloroform, and soluble in ethyl acetate and methanol. Its molecular weight is about 822.95 Da. Chemical names for rifampin include: 3-[[(4-methyl-1-piperazinyl)imino]-methyl]-rifamycin; or 5,6,9,17,19,21-hexahydroxy-23methoxy-2,4,12,16,18,20,22 heptamethyl-8-[N-(4-methyl-1-piperazinyl)formimidoyl]-2, 7-(epoxypentadeca[1,11,13]trienimino)naphtho[2,1-b] furan-1, 1 1 (2H)-dione 21-acetate.

Isoniazid is a hydrazide of isonicotinic acid. It is a colorless or white crystalline powder or white crystals. It is odorless and slowly affected by exposure to air and light. It is freely soluble in water, sparingly soluble in alcohol and slightly soluble in chloroform and in ether. Its molecular weight is about 137.14 Da and its chemical formula is $C_6H_7N_3O$. A chemical name for isoniazid is 4-pyridinecarboxylic acid, hydrazide.

Pyrazinamide, the pyrazine analogue of nicotinamide, is a white, crystalline powder, stable at room temperature, and sparingly soluble in water. The chemical name for pyrazinamide is pyrazinecarboxamide and its molecular weight is about 123.11 Da. Its chemical formula is $C_5H_5N_3O$.

Further names of these and other agents, can be found by reference to known manuals and websites (see, e.g., *Physicians' Desk Reference*, Medical Economics Co. (65$^{th}$ ed. 2011); United States Pharmacopeia (USP); PubMed Health).

Carbonic Anhydrase Inhibitors

Carbonic anhydrase inhibitors are a class of pharmaceuticals that suppress the activity of carbonic anhydrase. Their clinical use has been established as antiglaucoma agents, diuretics, antiepileptics, in the management of mountain sickness, gastric and duodenal ulcers, neurological disorders, or osteoporosis. These drugs include, at least, the following: acetazolamide (e.g. Diamox); brinzolamide (e.g. Azopt); dorzolamide (e.g. Trusopt); dorzolamide and timolol (e.g. Cosopt); and methazolamide (e.g. Neptazane).

Augmentin

Augmentin (amoxicillin/clavulanate potassium; also known as, for example, Augmentin; Augmentin 125-mg Chewable; Augmentin 200-mg Chewable; Augmentin 250-mg; Augmentin 250-mg Chewable; Augmentin 400-mg Chewable; Augmentin 500-mg; Augmentin 875-mg, among others) is an oral antibacterial combination consisting of the semisynthetic antibiotic amoxicillin and the β-lactamase inhibitor, clavulanate potassium (the potassium salt of clavulanic acid; also known as, for example, clavulanic acid or simply clavulanate). Augmentin belongs to a group of medications known as aminopenicillins, which is part of a larger group of medications known as beta-lactam antibiotics (named after the ring-like "lactam" structure of these antibiotics).

Amoxicillin (also known as, for example, Amoxicot, Amoxil, Dispermox, Moxatag, Moxilin, Senox, Sumox, Trimox, Wymox) prevents bacterial cell wall formation, which eventually causes the bacteria to die. However, many bacteria have developed resistance to amoxicillin and similar antibiotics by producing enzymes called beta-lactamases. Beta-lactamases break the beta-lactam ring, which may render amoxicillin and similar antibiotics ineffective. Accordingly, the other component of Augmentin, clavulanate potassium, is a beta-lactamase inhibitor. Clavulanate binds to bacterial beta-lactamase and stops the enzymes from breaking down the amoxicillin molecule. Essentially, clavulanate "augments" the activity of amoxicillin (hence the name Augmentin).

Further names of these and other agents, can be found by reference to known manuals and websites (see, e.g., *Physicians' Desk Reference*, Medical Economics Co. (65$^{th}$ ed. 2011); United States Pharmacopeia (USP); PubMed Health).

N-acetyl cysteine (NAC)

N-acetyl cysteine (NAC) It is an acetylated sulphur-containing amino-acid, and may be expected to cause the elementary bodies (EBs) of certain intracellular infectious organisms, such as chlamydia pneumoniae, to open prematurely, killing them.

Further names of these and other agents, can be found by reference to known manuals and websites (see, e.g., *Physicians' Desk Reference*, Medical Economics Co. (65$^{th}$ ed. 2011); United States Pharmacopeia (USP); PubMed Health).

Methods of Administering/Pharmaceutical Compositions

Administration of the compositions of this application can be accomplished via any mode of administration for therapeutic agents. These modes include systemic or local administration such as, but not limited to, oral, nasal, parenteral, transdermal, subcutaneous, vaginal, buccal, rectal or topical administration modes.

Depending on the intended mode of administration, the compositions can be in solid, semi-solid or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, they can also be administered in intravenous (both bolus and infusion), intraperitoneal, subcutaneous or intramuscular form, all using forms well known to those skilled in the pharmaceutical arts.

Illustrative pharmaceutical compositions are tablets and gelatin capsules comprising an inventive composition and a pharmaceutically acceptable carrier, such as, but not limited to: a) a diluent, e.g., purified water, triglyceride oils, such as, for example, hydrogenated or partially hydrogenated vegetable oil, or mixtures thereof, corn oil, olive oil, sunflower oil, safflower oil, fish oils, such as, but not limited to, EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as, by way of non-limiting example, glucose or beta-lactose, corn sweeteners, natural and synthetic gums such as, but not limited to, acacia, tragacanth or sodium alginate, waxes and/or polyvinylpyrrolidone, if desired; d) a disintegrant, e.g., starches, agar, methyl cellulose, bentonite, xanthan gum, alginic acid or its sodium salt, or effervescent mixtures; e) absorbent, colorant, flavorant and sweetener; f) an emulsifier or dispersing agent, such as, but not limited to, Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the compound such as, but not limited to, cyclodextrin, hydroxypropyl-cyclodextrin, PEG400, PEG200.

Liquid, particularly injectable, compositions can be prepared, for example, by dissolution, dispersion, etc. For example, the inventive composition is dissolved in or mixed with a pharmaceutically acceptable solvent such as, for example, water, saline, aqueous dextrose, glycerol, ethanol, and the like, to thereby form an injectable isotonic solution or suspension. Proteins such as, but not limited to, albumin, chylomicron particles, or serum proteins can be used to solubilize the fatty acid metformin derivatives.

The present compositions can be also formulated as a suppository that can be prepared from fatty emulsions or suspensions; using polyalkylene glycols such as, but not limited to, propylene glycol, as the carrier.

The present compositions can be also be administered in the form of liposome delivery systems, such as, but not limited to, small unilamellar vesicles, large unilamellar vesicles and multilamellar vesicles. Liposomes can be formed from a variety of phospholipids, containing cholesterol, stearylamine or phosphatidylcholines.

The present compositions can be also be delivered by the use of monoclonal antibodies as individual carriers to which the present compositions are coupled. The present compositions can be also be coupled with soluble polymers as targetable drug carriers. Such polymers can include polyvinylpyrrolidone, pyran copolymer, polyhydroxypropylmethacrylamide-phenol, polyhydroxyethylaspanamidephenol, or polyethyleneoxidepolylysine substituted with palmitoyl residues. Furthermore, the present compositions can be also be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

Parenteral injectable administration is generally used for subcutaneous, intramuscular or intravenous injections and infusions. Injectables can be prepared in conventional forms, either as liquid solutions or suspensions or solid forms suitable for dissolving in liquid prior to injection.

Compositions can be prepared according to conventional mixing, granulating or coating methods, respectively, and the present pharmaceutical compositions can contain from about 0.1% to about 80%, from about 5% to about 60%, or from about 1% to about 20% of the present compositions by weight or volume.

The dosage regimen utilizing the present compositions may be selected in accordance with a variety of factors including type, species, age, weight, sex and medical condition of the patient; the severity of the condition to be treated; the route of administration; the renal or hepatic function of the patient; and the composition employed. A physician or veterinarian of ordinary skill in the art can readily determine and prescribe the effective amount of the drug required to prevent, counter or arrest the progress of the condition.

Effective dosage amounts of the present invention, when used for the indicated effects, can range from about 25-1000 mg per day. Compositions for in vivo or in vitro use can contain about 20, 50, 75, 100, 150, 250, 500, 750, 1,000, 1,250, 2,500, 3,500, or 5,000 mg of the inventive compounds. In one embodiment, the dosage amounts of the present invention are 400 mg Tetracycline and 1000 mg Macrolide. In one embodiment, the compositions are in the form of a tablet that can be scored. Appropriate dosages can be determined as set forth in Goodman, L. S.; Gilman, A. *The Pharmacological Basis of Therapeutics,* 5th ed.; MacMillan: New York, 1975, pp. 201-226.

The present compositions can be administered in a single daily dose, or the total daily dosage can be administered in divided doses of two, three or four times daily. Furthermore, they can be administered in intranasal form via topical use of suitable intranasal vehicles, or via transdermal routes, using those forms of transdermal skin patches well known to those of ordinary skill in that art. To be administered in the form of a transdermal delivery system, the dosage administration can be continuous rather than intermittent throughout the dosage regimen. Other illustrative topical preparations include creams, ointments, lotions, aerosol sprays and gels.

EXAMPLES

Example 1: Treatment of Neurological and/or Neurodegenerative Disorders with Biaxin, Minocycline, Vitamin D, and Cod Liver Oil Five patients were treated over a long course of time with the combination therapy of Biaxin, minocycline, vitamin D, and cod liver oil. All of the patients showed marked improvement in their neurological and/or neurodegenerative discomforts.

In one case, the patient was an 81 year old male that was monitored and treated over a 14 year period. The patient presented with tremors, balance problems, and early cognitive impairment. The patient was diagnosed with Alzheimer's Disease symptoms by two independent doctors, including the inventors. The patient was further diagnosed with macular degeneration. The patient also showed signs of inclusion body myositis which suggests systemic amyloid disease. Ocular observations were made. Fibrils and spokes in both eyes suggesting supranuclear cataracts were seen. Also, the patient displayed nuclear cataracts, optic disc cupping, drusen in the retina, retinitis pigmentosa with cystoid macular edema, decreased macular volume and thinning of the nerve fiber layer. The inventors reviewed MRI tests conducted by others which indicated atrophy and small vessel disease. Initial blood tests showed elevated inflammatory markers including c-reactive protein, homocysteine, accelerated sedimentation rate, and elevated beta-2-microglobulin. IgG titers showed that the following infections were active: Lyme disease, Chlamydia pneumoniae, and Q-fever. The patient was treated with a combination treatment of Biaxin, minocycline, vitamin D, and cod liver oil. Specifically, 200 mg minocycline and 1000 mg Biaxin (chlarithromycin)/day were administered as two doses of half the total amount (i.e. 100 mg minocycline and 500 mg Biaxin (chlarithromycin)). Doses were administered in the morning and the evening. The dose of Vitamin D was 5000 units taken in either the morning or the evening, depending on patient preference. The dose of cod liver oil was 15 grams taken in either the morning or the evening, depending on patient preference. The patient was initially treated for 6 months and re-examined; treatment was extended for a longer period because of continued infection. After the initial 6 months, all indications of tremors ceased and balance issues also resolved. Further, the patient no longer required a walker for regular mobility. In addition, muscle strength improved as determined by his walking ability. Over the course of a year, the patient's memory was stable with possible subjective improvement as communicated by his wife (recorded on video). Patient's hearing also improved as shown through auditory examination. After 1 year of treatment, the patient ceased the continuous use of hearing aids that he used in both ears. His vision also objectively improved. This was noted over a 4-year period.

In another case, the patient was an 84 year old male that was monitored and treated over a 4 year period. The patient presented with severe memory deficiency, severe cognitive function issues, tremors, balance problems, muscle mass loss, and severe vision loss. The patient was diagnosed with Alzheimer's Disease symptoms by two independent doctors, including the inventors. The patient also showed signs of inclusion body myositis, suggesting systemic amyloid disease. Ocular observations were made. Fibrils and spokes in both eyes suggesting supranuclear cataracts were seen. Also, the patient displayed nuclear cataracts, optic disc cupping, drusen in the retina, decreased macular volume and thinning of the nerve fiber layer, decayed visual field, and decreased blood flow in the retina as determined by Doppler measurements. The inventors reviewed MRI tests conducted by others which indicated atrophy and small vessel disease. Initial blood tests showed elevated inflammatory markers including c-reactive protein, accelerated sedimentation rate, and elevated beta-2-microglobulin. IgG titers showed that toxoplasmosis and Chlamydia pneumoniae infections were active. The patient was treated with a combination treatment of Biaxin, minocycline, vitamin D, and cod liver oil. Specifically, 200 mg minocycline and 1000 mg Biaxin (chlarithromycin)/day were administered as two doses of half the total amount (i.e., 100 mg minocycline and 500 mg Biaxin (chlarithromycin)). Doses were administered in the morning and the evening. The dose of Vitamin D was 5000 units taken in either the morning or the evening, depending on patient preference. The dose of cod liver oil was 15 grams taken in either the morning or the evening, depending on patient preference. The patient was initially treated for 6 months and re-examined; treatment was extended for a longer period. After the initial 6 months, patient's memory significantly improved as shown in video and as represented by family members (recorded on video). Patient's ability to communicate, understand, and complete thoughts significantly improved. Also, all indications of tremors ceased and balance issues also resolved. In addition, muscle strength improved as determined by walking ability. Vision also objectively improved. This was noted over a 2-year period. Further tests of the patient showed that blood test values returned to normal range. Additionally, there is clear evidence that the supranuclear cataracts diminished in size over two years of treatment.

In another case, the patient was an 67 year old female that was monitored and treated over a 3 year period. The patient presented with memory deficiency and severe vision loss. The patient was diagnosed with Alzheimer's Disease symptoms by two independent doctors, including the inventors. The patient was also diagnosed with macular degeneration. Ocular observations were made. Early fibrils that are precursors of supranuclear cataracts were seen. Also, patient displayed optic disc cupping, drusen in the retina, thinning of the nerve fiber layer, delayed visual evoked response, and decayed visual field. The inventors reviewed MRI tests conducted by others which indicated atrophy and small vessel disease. Initial blood tests showed elevated inflammatory markers including c-reactive protein, accelerated sedimentation rate, and elevated beta-2-microglobulin. IgG titers showed that a Chlamydia pneumoniae infection was active. The patient was treated with a combination treatment of Biaxin, minocycline, vitamin D, and cod liver oil. Specifically, 200 mg minocycline and 1000 mg Biaxin (chlarithromycin)/day were administered as two doses of half the total amount (i.e. 100 mg minocycline and 500 mg Biaxin (chlarithromycin)). Doses were administered in the morning and the evening. The dose of Vitamin D was 5000 units taken in either the morning or the evening, depending on patient preference. The dose of cod liver oil was 15 grams taken in either the morning or the evening, depending on patient preference. The patient was initially treated for 6 months and re-examined; treatment was extended for a longer period. After the initial 6 months, patient's memory significantly improved as represented by family members and visual evoked responses which showed improvements. Patient's vision also objectively improved, including visual acuity and visual field. Also, visual fixation improved over the course of treatment. This was noted over a 3-year period. Further tests of the patient showed that blood test values returned to normal range. Additionally, visual evoked response showed that brain function improved over time and the ability to concentrate improved as indicated by fixation measurements. Visual acuity also improved.

In another case, the patient was an 83 year old male that was monitored and treated over a 12 year period. The patient presented with memory deficiency, severe vision loss, and tremors. The patient was diagnosed with Alzheimer's Disease and macular degeneration by two independent doctors, including the inventors. The patient also showed signs of fibrils that are precursors of supranuclear cataracts. Patient also had optic disc cupping, optic neuritis (optic nerve thinning), thinning of the nerve fiber layer, delayed visual evoked response, and decayed visual field. The inventors reviewed MRI tests conducted by others which indicated atrophy and small vessel disease. Initial blood tests showed elevated inflammatory markers including c-reactive protein, homocysteine, accelerated sedimentation rate, and elevated beta-2-microglobulin. IgG titers showed that a Chlamydia pneumoniae infection was active. The patient was treated with a combination treatment of Biaxin, minocycline, vitamin D, and cod liver oil. Specifically, 200 mg minocycline and 1000 mg Biaxin (chlarithromycin)/day were administered as two doses of half the total amount (i.e. 100 mg minocycline and 500 mg Biaxin (chlarithromycin)). Doses were administered in the morning and the evening. The dose of Vitamin D was 5000 units taken in either the morning or the evening based on patient preference. The dose of cod liver oil was 15 grams taken in either the morning or the evening based on patient preference. It is noted that this patient was administered half doses of the above, according to the same regiment, for the first month of treatment. The patient was initially treated for 6 months and re-examined; treatment was extended for a longer period because of continued infection. After the initial 6 months, the patient's memory improved as represented by family members. Further, patient's vision also objectively improved including visual acuity and visual field. At the beginning of treatment the patient could no longer read and could not play golf but, thirteen years later, the patient engages in both activities regularly and still drives an automobile. Blood tests values also returned to normal range. Additionally, the ability to concentrate improved as indicated by fixation measurements. Visual acuity also improved significantly. Optic nerve showed recovery in both volume and thickness by MRI over a 2-year period.

In still another case, the patient was an 85 year old male that was monitored and treated over a 11 year period. The patient presented with memory deficiency, severe vision loss, and tremors. The patient was diagnosed with Alzheimer's Disease and macular degeneration by two independent doctors, including the inventors. The patient also presented cortical/supranuclear cataracts. Patient also had optic disc cupping, optic neuritis (optic nerve thinning), drusen in the retina, thinning of the retinal nerve fiber layer, delayed visual evoked response, decayed visual field, decreased retinal blood flow (as observed by Doppler measurement), low tension glaucoma, and cortical cataracts. The inventors reviewed MRI tests conducted by others which indicated atrophy and small vessel disease/ischemia. Initial blood tests showed elevated inflammatory markers including c-reactive protein, homocysteine, accelerated sedimentation rate, and elevated beta-2-microglobulin. IgG titers showed that chlamydia pneumoniae and Lyme disease infections were active. The patient was treated with a combination treatment of Biaxin, minocycline, vitamin D, and cod liver oil. The patient was initially treated for 6 months and re-examined; treatment was extended intermittently for a further 11 years. After 1 year, the patient's memory improved as represented by family members. Further, the patient's vision also objectively improved including visual acuity and visual field. Shaking/tremors also abated in the first 6 months. Constricted field improved as did retinal blood flow. Optic neuritis improved per optical coherence tomography (OCT) measurement. Prior to treatment the patient could not remember phone numbers or names of family members. After eleven years, patient's memory is superior for his age. Thus, mental acuity actually increased over treatment period. Blood tests values also returned to normal range. Additionally, the ability to concentrate improved as indicated by fixation measurements. Visual acuity also improved significantly. For instance, the optic nerve showed recovery per OCT testing. Visual evoked response (VER) showed slight improvement. Further, cortical cataracts diminished in size during 11 years of treatment.

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

INCORPORATION BY REFERENCE

All patents and publications referenced herein are hereby incorporated by reference in their entireties.

What is claimed is:
1. A pharmaceutical composition comprising an effective amount of minocycline, an effective amount of roxithromycin, and an effective amount of an agent selected from vitamin D, cod liver oil, Augmentin, Diamox, Rifater and N-acetyl cysteine (NAC) and combinations of two or more thereof.

2. The pharmaceutical composition of claim 1, wherein the compositions further comprises excipients, wherein the compositions further comprises single or multiple unit capsules, single or multiple unit tablets, single or multiple unit suspensions, or single or multiple unit emulsions.

3. The pharmaceutical compositions of claim 1, wherein active ingredients are either mixed together in a tablet, capsule, suspension, or emulsion, or wherein active ingredients are partitioned.

* * * * *